US006648844B2

(12) United States Patent
Kamerman

(10) Patent No.: US 6,648,844 B2
(45) Date of Patent: Nov. 18, 2003

(54) APPARATUS AND METHOD FOR DECOMPRESSING INVERTEBRAL DISCS, RELIEVING BACK PAIN, AND PROMOTING BACK HEALING

(76) Inventor: Brett Kamerman, 310 Montero Ave., Newport Beach, CA (US) 92661

( * ) Notice: Subject to any disclaimer, the term of this patent is extended or adjusted under 35 U.S.C. 154(b) by 0 days.

(21) Appl. No.: 10/138,733

(22) Filed: May 3, 2002

(65) Prior Publication Data

US 2003/0009121 A1 Jan. 9, 2003

Related U.S. Application Data

(60) Provisional application No. 60/288,514, filed on May 3, 2001.

(51) Int. Cl.[7] .............................. A61H 1/02; A61F 5/00

(52) U.S. Cl. .............................................. 602/36; 602/32

(58) Field of Search .......................... 602/32–37, 38–40, 602/4

(56) References Cited

U.S. PATENT DOCUMENTS 1,994,593 A * 3/1935 Schmidt ...................... 482/72
3,767,191 A * 10/1973 Riley .......................... 482/25
3,871,366 A * 3/1975 Cotrel ......................... 602/33
3,960,146 A * 6/1976 Albrecht ...................... 602/36
4,073,290 A * 2/1978 Farrar, Jr. .................... 602/36
4,407,274 A * 10/1983 Goodley ...................... 606/241
4,580,554 A * 4/1986 Goodley ...................... 606/201
4,647,035 A * 3/1987 Yellen .......................... 482/72
4,865,022 A * 9/1989 Gorsen ........................ 602/33
4,971,043 A * 11/1990 Jones .......................... 602/36
5,285,017 A * 2/1994 Gardner ...................... 174/261
5,431,617 A * 7/1995 Rattray, Jr. ................. 482/129
5,549,532 A * 8/1996 Kropp ........................ 482/126
5,669,864 A * 9/1997 Brister ....................... 482/132
5,895,367 A * 4/1999 Mautoni ...................... 602/32
6,258,050 B1 * 7/2001 Henderson ................... 602/33

* cited by examiner

*Primary Examiner*—Nicholas D. Lucchesi
*Assistant Examiner*—Huong Q. Pham
(74) *Attorney, Agent, or Firm*—Thompson & Knight LLP

(57) ABSTRACT

An apparatus and method for decompressing invertebral discs, relieving back pain, and promoting back healing is provided, involving a pelvic harness, elastic member, and foot-pad-pressing unit. The pelvic harness has a back side and a front side. The back side of the pelvic harness is connected to the elastic member's top end. The elastic member's bottom end is connected to the foot-pad-pressing unit. The foot-pad-pressing unit has a centrally located connector receptacle. The centrally located connector receptacle is used to attach the bottom end of the elastic member to the foot-pad-pressing unit.

1 Claim, 4 Drawing Sheets

APPARATUS AND METHOD FOR DECOMPRESSING INVERTEBRAL DISCS, RELIEVING BACK PAIN, AND PROMOTING BACK HEALING

CROSS-REFERENCE TO RELATED APPLICATIONS

This application claims the benefit of the following U.S. Provisional Application, which is hereby incorporated by reference:

| Ser. No. | Title | Filing Date |
|---|---|---|
| 60/288,514 | An Apparatus and Method for Decompressing Intervertebral Discs, Relieving Back Pain, and Promoting Back Healing | May 3, 2001 |

FIELD OF THE INVENTION

The present invention relates to an apparatus and method for decompressing intervertebral discs, relieving back pain, and promoting back healing.

BACKGROUND OF THE INVENTION

Because of numerous factors relating to lifestyle and environment, the back and spine tend to wear out faster than other parts of the body. The back and spine injure easily and become a source of pain for a large percentage of people at some point in their lives.

The source of the pain can be traced to the intervertebral discs found in the back between the vertebrae. These discs consist of a nonbone, cartilage-type material shaped somewhat like a donut, the center of which is filled with a viscous, fluid-like, gelatinous material. The purpose of the disc is to act as a shock absorber between the hard bony vertebrae. If the discs did not exist, the bony vertebra would rest directly upon one another, and any shock to the body would result in a fracture when one vertebra hit another.

The discs, working in association with the joints of the back (called apophyseal joints), keep the nerves unobstructed throughout the spine. Due to age, use, injury, or other factors, the discs can become less effective, less efficient, or even damaged. Damage to the discs may result in several conditions including herniated disc, slipped disc, degenerative disc disease, ruptured disc, and compressed disc.

Patients may suffer from neurocompression—a condition associated with the damaged disc and posterior facet syndrome. The characteristics of the damage are that the outer portion of the disc cracks and the inner gel escapes into the area of the nerve. When this occurs, the disc exhibits a loss of moisture, becoming dehydrated. Then, instead of protecting the integrity of the nerve, the disc invades the area that the nerve inhabits, impinging upon or rubbing against the tunnel in which the nerve travels, or actually pinching the nerve. This is the cause of the pain.

The pain can be localized at the location of the damaged disc, or the pain can travel down the route of the nerve, causing referred pain wherever the nerve travels. Sciatica is the term for the referred pain down the nerve of the leg, which is called the sciatic nerve. Similar referred pain can occur in the arms as well. The spine consists of the entire nerve center for the body, so any interruption or antagonism of the components of this nerve center will cause uneasiness to the human body, and this uneasiness will manifest as pain.

People may experience moderate to extreme pain, depending on the severity of the nerve impingements. It appears that most of this type of pain can be attributed to the intrusion of the damaged disc upon the nerve.

When a disc is damaged, it becomes dehydrated and shrinks from its original healthy size, compromising the integrity and effectiveness of the disc. The disc in this state is compressed; therefore, if the disc can be decompressed and returned to its normal healthy state, the problem (i.e., pain) can be reduced.

Pain may also have an emotional effect on the sufferer. Emotional pain is a nonphysical pain that is manifested physically, known as stress. Stress has been related to severe health problems including heart attacks, evidencing the power that stress has on the human body. This stress causes those with back pain to experience both an increased level of physical pain and increased risk of other health problems.

The intensified pain can cause a downward spiral of pain and stress as each feed upon the other. Stress causes a human being to tense the muscles, and the tense muscles contribute to the pressure that the disc exerts on the nerve, thereby causing more pain and more intense pain. If the original pain can be eliminated, then the downward spiral of pain can be interrupted.

Back pain may cause more stress than other pain because the pain is inside and is not an obvious disability, as are other types of injury such as a broken arm. Human beings are social and value feedback from others. If a person breaks a bone in an arm, and the arm is set in a cast, then others who see the cast typically ask about the injury and offer support and sympathy. Even complete strangers who see the cast recognize the pain associated with this condition.

On the other hand, while back pain can be more severe than the pain associated with a broken arm, a back condition is not obvious or easily observed. The patient's acquaintances may tend to deny the validity of the pain and may minimize the back patient's genuine discomfort. As a result, they may not offer support or sympathy, and may even increase the patient's stress by suggesting that the patient is simply a complainer. Even if such comments are not articulated, the patient may feel as if others view the condition with skepticism.

Depression also may result from the back pain and the accompanying stress. A back patient may feel frustration, insignificance, hopelessness, dependency, self-doubt, and desperation. In addition, back patients often tire of making excuses for not attending events, refuse to try new activities, and feel as if life is passing them by.

A patient may not remember a time without pain and may become inactive, unproductive, and resentful of others who are pain-free. The patient may even begin to question if the pain is really there.

A back injury, unlike a broken arm, cannot be effectively immobilized and given time to heal. Instead, it must be used daily for almost every task, and it gets rest only when the patient attempts to sleep. Effective sleeping is often impossible, however, because of the severe pain. Some patients can fall asleep only with drugs or only after struggling with the pain until exhausted. Like a broken arm, a damaged disk needs to be immobilized and given time to heal itself.

Unlike the prior art, the present invention does not require the patient to have the assistance of another person or a computer. Additionally, the present invention is much more affordable than any of the prior art. The present invention is easier to transport than the prior art.

SUMMARY OF THE INVENTION

One object of the present invention is to provide a home device that meets the needs described above.

Another object of the present invention is to reduce or eliminate the need for the patient to have the assistance of another person or a computer.

Another object of the present invention is to provide an affordable treatment solution.

Another object of the present invention is to provide a treatment device that is easier to transport than the prior art.

The foregoing objects, and other improvements and advantages, are achieved as is now described. The invention provides a new and improved apparatus for decompressing invertebral discs. One embodiment for the invention includes a pelvic harness having a back side and a front side. There is also an elastic member having a bottom end and a top end, where the top end of the elastic member is coupled to the back side of the pelvic harness. Lastly, there is a foot-pad-pressing unit having an upward-facing surface, a downward-facing surface, and at least one centrally located connector receptacle where the bottom end of the elastic member is engaged.

Other embodiments for the invention are: (1) the pelvic harness as a support belt; (2) the pelvic harness as a support belt and the elastic member as a bungee cord; (3) the pelvic harness as a support belt, and the elastic member as a bungee cord, and the foot-pad-pressing unit as a rigid metallic sheet; (4) the foot-pad-pressing unit as a rigid metallic sheet; (5) the elastic member as a bungee cord; (6) a rolling mechanism attached to the downward-facing surface for rolling facilitation during use of the apparatus; (7) a rolling mechanism attached to the downward-facing surface along with a bungee cord as the elastic member; (8) the foot-pad-pressing unit as a rod; (9) the foot-pad-pressing unit as a rod with a left side and a right side and including a right-foot shell and a left-foot shell (attached to their respective sides of the rod); (10) at least one foot strap for each of the foot shells (both the right-foot shell and the left-foot shell) for use with the rod as the foot-pad-pressing unit; (11) the elastic member as a metallic spring; (12) the foot-pad-pressing unit as a metallic sheet that is substantially elliptical; (13) the footpad-pressing unit as a metallic sheet that is substantially rectangular; (14) the elastic member as a rubber-based material; (15) the elastic member as a flat rubber strap; (16) the elastic member as a rubber-based material and a rolling mechanism attached to the downward-facing surface of the foot-pad-pressing unit; (17) the downward-facing surface being smooth and rounded; (18) a rolling mechanism attached to the downward-facing surface of the foot-pad-pressing unit and a support belt for use as the pelvic harness.

Another embodiment of the invention is disclosed as an apparatus for decompressing invertebral discs that includes a pelvic harness (having a support belt having a back side, a front side, and a connecting mechanism affixed to the backside of the support belt) and a pelvic-harness connector (having a looped end and a studded end where the looped end is removably connected to the connecting mechanism of the support belt). This same embodiment also contains: (1) a metallic spring having a bottom end and a top end where the top end is secured to the studded end of the pelvic-harness connector; (2) a pressing-unit connector that has a studded end (which is secured to the bottom end of the metallic spring), and an adjusting end (which has a beginning-threaded end and a stopping-threaded end where the stopping-threaded end begins midway along the pressing-unit connector); (3) a foot-pad-pressing unit having a rigid metal sheet (that is substantially rectangular and having at least one pressing-unit connector receptacle, a top side, an under side, an upward-facing surface, a downward-facing surface, and at least one centrally located connector receptacle where the adjusting end of the pressing-unit connector is engaged) and an adjusting means (having an upper turn-bolt positioned on the stopping-threaded end of the pressing-unit connector and adjacent to the top side of the metal sheet, and a lower turn-bolt positioned on the beginning-threaded end of the pressing unit and adjacent to the under side of the metal sheet); (4) a rolling mechanism attached to the downward-facing surface of the rigid metal sheet to facilitate movement along a surface during use.

A method of decompressing invertebral discs is disclosed. This method focuses on the use of one leg and its corresponding foot. The method includes several steps. First, the person puts on a traction apparatus that includes a foot-pad-pressing unit. Next, the person lies face up on the floor while wearing the traction apparatus. Then the person places a foot on the foot-pad-pressing unit. The person then exerts force against the foot-pad-pressing unit with the foot until the leg is fully extended. Next, the person assumes a position by slightly bending the leg's knee. The person holds this position for a prescribed amount of time. Last, the person relaxes the leg allowing the foot-pad-pressing unit to return to its original position. The person repeats the pressing and relaxing steps as prescribed.

Another method of decompressing invertebral discs is disclosed as well. This is very similar to the above method. But this method focuses on the use of two legs and two feet. First, the person puts on a traction apparatus that includes a foot-pad-pressing unit. Next, the person lies face up on the floor while wearing the traction apparatus. Then the person places both feet on the foot-pad-pressing unit. The person then exerts force against the foot-pad-pressing unit with both feet until both legs are fully extended. Next, the person assumes a position by slightly bending both knees. The person holds this position for a prescribed amount of time. Last, the person relaxes both legs allowing the foot-pad-pressing unit to return to its original position. The person repeats the pressing and relaxing steps as prescribed.

For a better understanding of the present invention, together with other and further objects thereof, reference is made to the following description, taken in conjunction with the accompanying drawings, and the invention's scope will be pointed out in the pending claims.

BRIEF DESCRIPTION OF THE DRAWINGS

Other objects and advantages of the invention will become apparent upon reading the following detailed description and upon referring to the accompanying drawings, in which.

DESCRIPTION OF THE INVENTION

Figure 1:
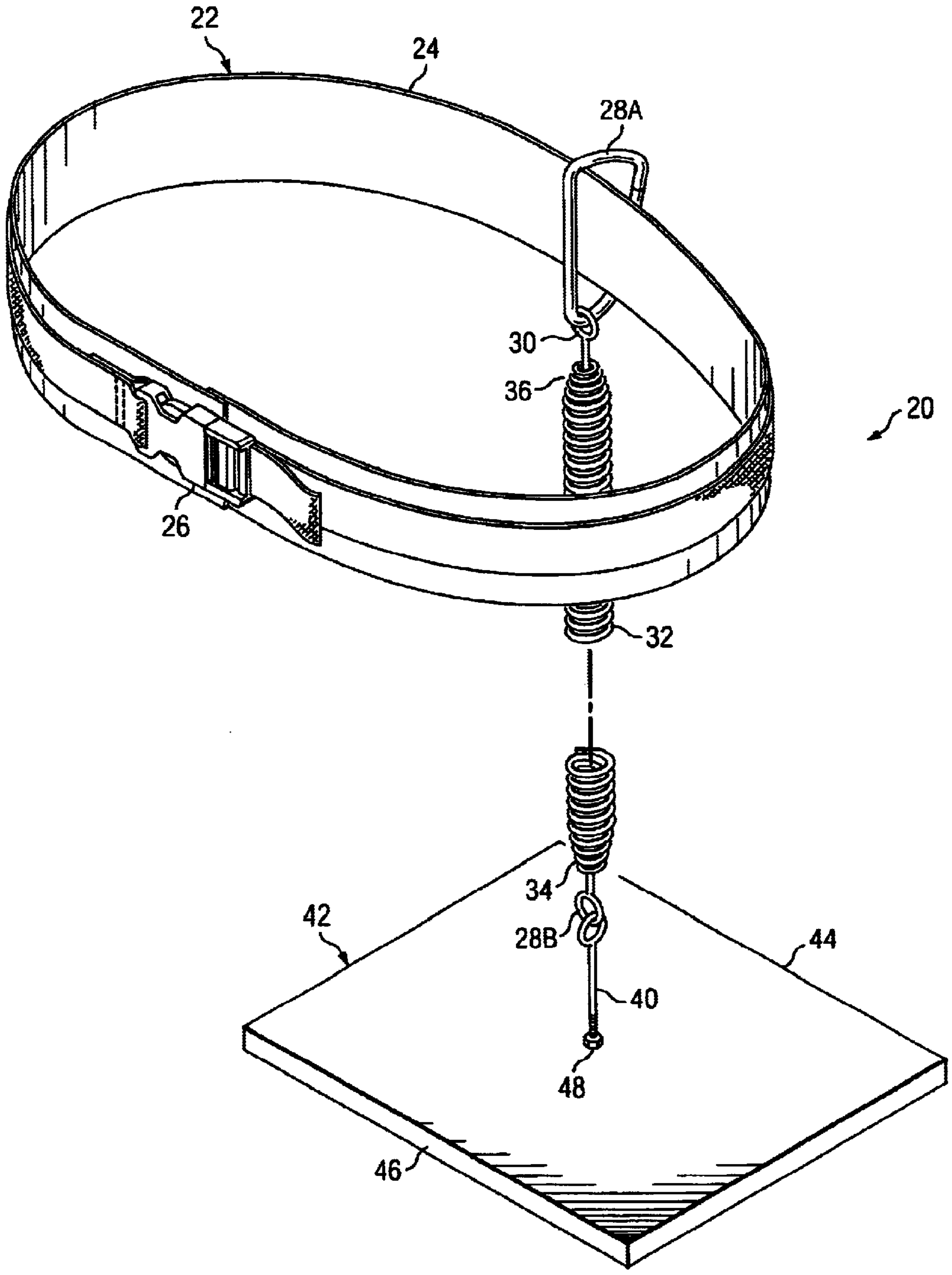
FIG. 1 is a simplified schematic diagram of a first embodiment of the present invention.

FIG. 1 is a drawing of a first embodiment of the invention 20. It shows a pelvic harness 22 (the term "pelvic harness 22" is used to refer to this element of the invention, which may also be, for example, a leather strap, or any flexible material that can accommodate a buckling mechanism) having a first connecting mechanism 28A (the term "first connecting mechanism 28A" is used to refer to this element of the invention, which may also be, for example, a hook and loop system, a buckling mechanism, Velcro, a clamp, a carabiner, a link, or a tie) positioned on the back side 24 of the pelvic harness 22. A top end 36 of an elastic member 32 (the term "elastic member 32" is used to refer to this element of the invention, which may also be, for example, a metallic spring, a rubber strap, a bungee cord, or a rubber-based material) includes a pelvic-harness connector 30. The pelvic-harness connector 30 connects to the first connecting mechanism 28A of the pelvic harness 22. The bottom end 34 of the elastic member 32 includes a second connecting mechanism 28B (the term "connecting mechanism 28B" is used to refer to this element of the invention, which may also be, for example, a hook and loop system, a buckling mechanism, Velcro, a clamp, a carabiner, a link, or a tie) that is linked to a pressing-unit connector 40. The pressing-unit connector 40 attaches to a foot-pad-pressing unit 42 by engaging a centrally located connector receptacle 48 (the centrally located connector receptacle may be, for example, a groove, a hole, or an insert). The pelvic-harness connector 30, first connecting mechanism 28A, second connecting mechanism 28B, and pressing-unit connector 40 can be (1) part of the elastic member 32 material; or (2) strappings attached to the elastic member 32. The foot-pad-pressing unit 42 may be, for example, a metal sheet, a rod, hardened plastic, wood, stone, or some other rigid material. The shape of the foot-pad-pressing unit 42 may be, for example, elliptical, circular, rectangular, or square. In this particular embodiment, the pelvic harness 22 is implemented with a support belt, the first connecting mechanism 28A is implemented with a carabiner, and the elastic member 32 is implemented with a metallic spring.

Figure 2A:
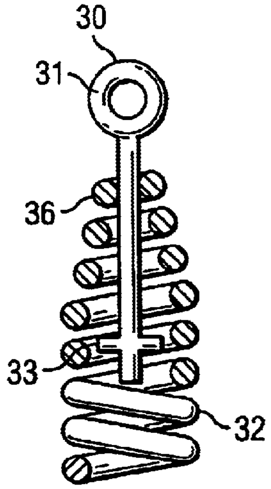
FIG. 2A is a perspective view of a pelvic-harness connector that may be used in the apparatus of FIG. 1.

FIG. 2A is a drawing of a top end 36 of an elastic member 32 including a corresponding pelvic-harness connector 30. The pelvic-harness connector 30 has a looped end 31 and a studded end 33. The studded end 33 is permanently engaged in the elastic member 32. The looped end 31 is removably connectable to the connecting mechanism 28 (shown in FIG. 1) of the pelvic harness 22 (shown in FIG. 1).

Figure 2B:
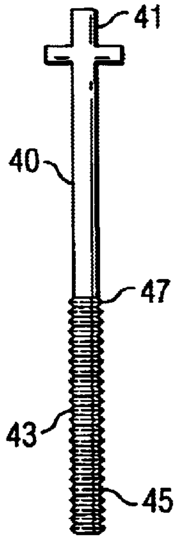
FIG. 2B is a perspective view of a pressing-unit connector that may be used in the apparatus of FIG. 1.

FIG. 2B is a drawing of a pressing-unit connector 40. The pressing-unit connector 40 has a connecting end 41 and an adjusting end 43. The adjusting end 43 has a beginning threaded end 45 and a stopping threaded end 47. The stopping threaded end 47 is located midway along the pressing-unit connector.

Figure 2C:
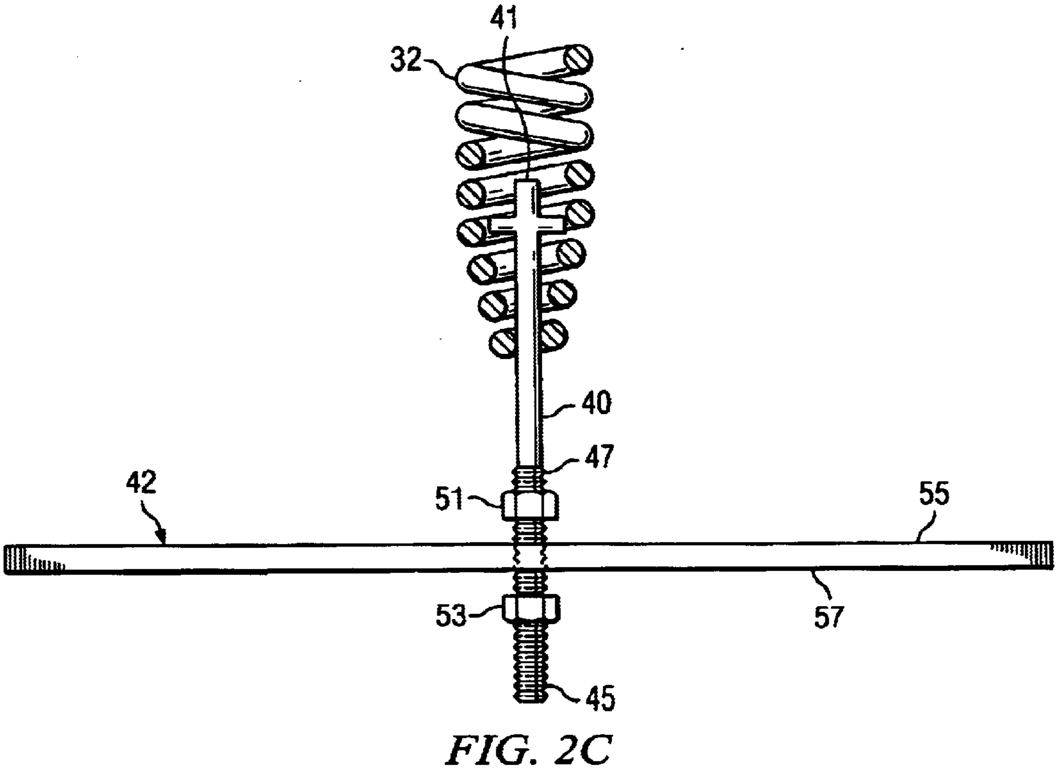
FIG. 2C is a perspective view of a foot-pad-pressing unit that is adjustably connected to an elastic member by a pressing-unit connector a unit that may be used in the apparatus of FIG. 1.

FIG. 2C is a drawing of a foot-pad-pressing unit 42 adjustably connected to an adjusting end 43 (shown in FIG. 2B) of the pressing-unit connector 40 by an upper turn-bolt 51 and a lower turn-bolt 53. The upper turn-bolt 51 is adjacent to the top side 55 of the foot-pad-pressing unit 42. The lower turn-bolt 53 is adjacent to the under side 57 of the foot-pad-pressing unit 42. The upper turn-bolt 51 and the lower turn-bolt 53 are both threaded onto the adjusting end 43 (shown in FIG. 2B) of the pressing-unit connector 40. The upper turn-bolt 51 and the lower turn-bolt 53 can be cotter pins. The pressing-unit connector 40 is connected to the elastic member 32 by the connecting end 41 of the pressing-unit connector 40 (shown in FIG. 2B).

Figure 3A:
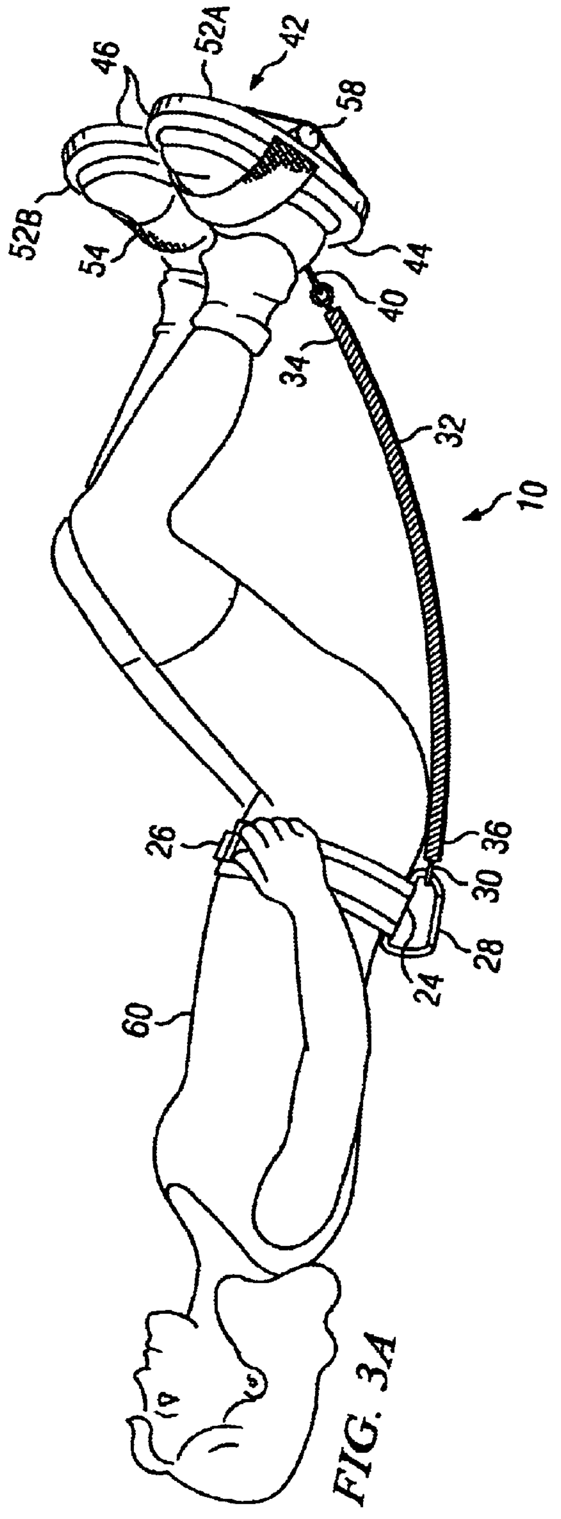
FIG. 3A is a perspective view of a patient using an embodiment of the present invention.
Figure 3B:
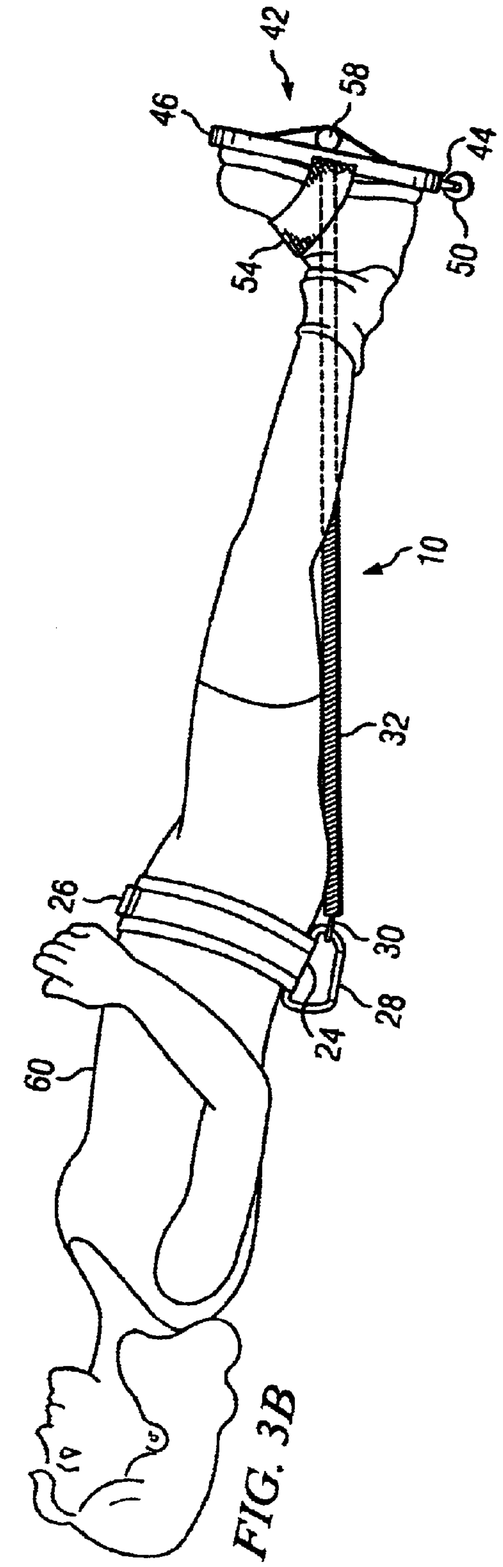
FIG. 3B is another perspective view of a patient using an embodiment of the present invention.

FIGS. 3A and 3B are drawings of the apparatus 20 (shown in FIG. 1) being used according to the claimed method 10. They show a patient 60 lying down on his back while wearing an embodiment of the claimed invention 20 (shown in FIG. 1). FIGS. 3A and 3B show the foot-pad-pressing unit 42 having a rod 58 as the base for the foot-pad-pressing unit 42. FIG. 3A shows a right-foot shell 52A and a left-foot shell 52B—each of which is connected to the corresponding side of the rod 58. FIG. 3B shows the foot-pad-pressing unit 42 having a downward facing surface 44 with a rolling mechanism 50 attached to it. The rolling mechanism may be, for example, wheels, ball bearings, or a rolling-pin type mechanism. The FIGS. 3A and 3B also show foot straps 54 connected to the right-foot shell 52A (shown in FIGS. 3A and 3B) and the left-foot shell 52B (shown in FIG. 3A) on the pressing-unit connector 40 (shown in FIG. 3A).

Figure 4:
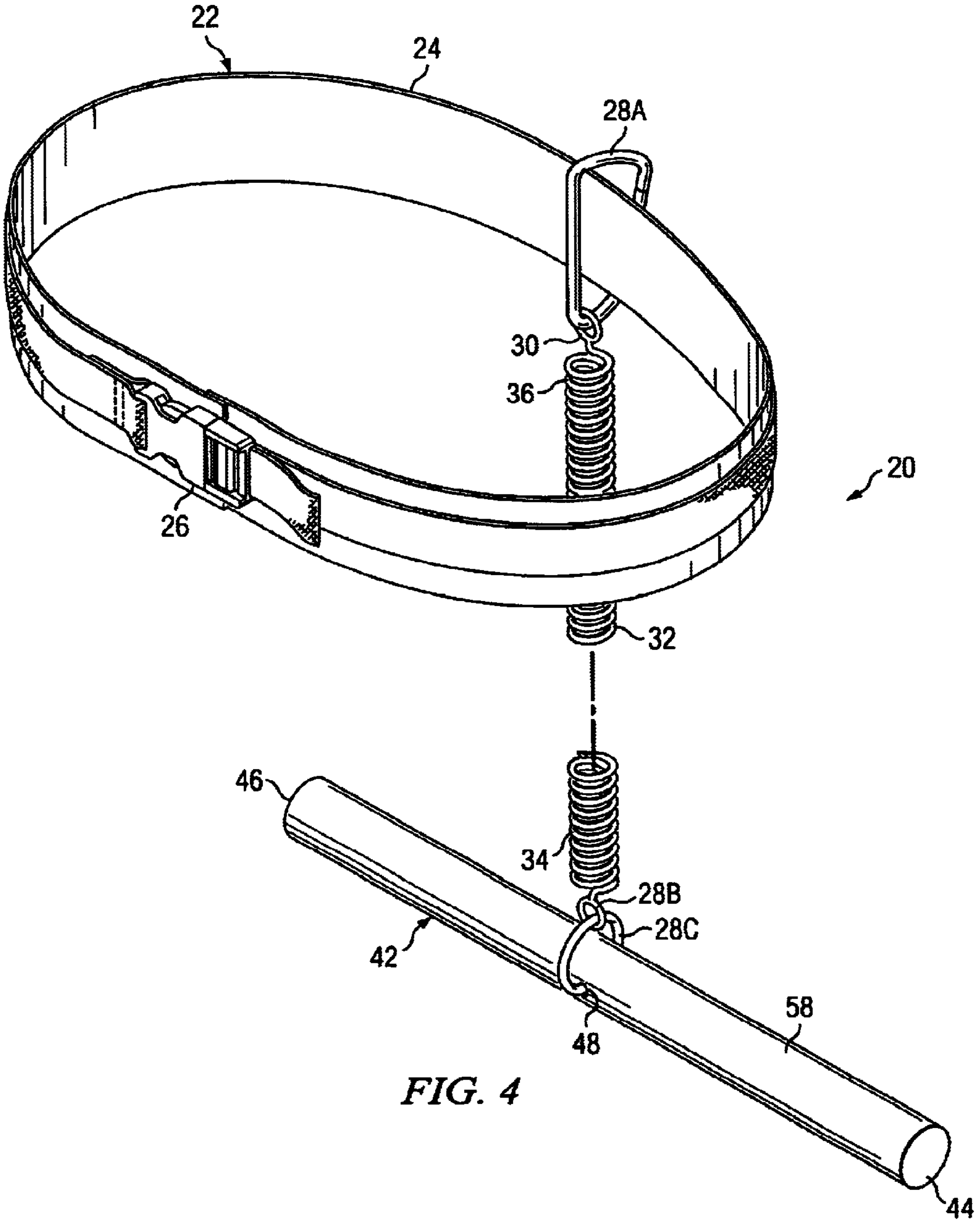
FIG. 4 is a simplified schematic diagram of another embodiment of the present invention.

FIG. 4 is a drawing of another embodiment of the invention 20. It shows a pelvic harness 22 having a first connecting mechanism 28A positioned on the back side 24 of the pelvic harness 22. The top end 36 of an elastic member 32 (the term "elastic member 32" is used to refer to this element of the invention, which may also be, for example, a metallic spring, a rubber strap, a bungee cord, or a rubber-based material) includes a pelvic-harness connector 30. The pelvic-harness connector 30 connects to the first connecting mechanism 28A of the pelvic harness 22. The bottom end 34 of the elastic member 32 includes a second connecting mechanism 28B that is linked to a third connecting mechanism 28C. The third connecting mechanism 28C attaches to a foot-pad-pressing unit 42 by engaging a centrally located connector receptacle 48 (the centrally located connector receptacle 48 may be, for example, a groove, a hole, or an insert). The foot-pad-pressing unit 42 may be, for example, a metal sheet, a rod, hardened plastic, wood, stone, or some other rigid material. It may also be an integral extension of the elastic member 32. The shape of the foot-pad-pressing unit 42 may be, for example, elliptical, circular, rectangular, or square.

The bottom of the elastic member 32 can be designed so that the elastic member 32 and the foot-pad-pressing unit 42 are a single unit. The entire device 20 can be made of one piece. At one end, elastic member 32 can be crafted into a pelvic harness, and at the other end, elastic member 32 can be crafted into a foot-pad-pressing unit 42.

While this section describes what are believed to be the preferred embodiments of the present invention, those skilled in the art will recognize that other and further changes and modifications may be made thereto without departing from the spirit of the invention, and this application is intended to claim all such changes and modifications that fall within the scope of the invention.

The invention claimed is:

1. An apparatus for decompressing invertebral discs, relieving back pain, and promoting back healing comprising:

a pelvic harness having a support belt and a connecting mechanism, the support belt having a back side and a front side, the connecting mechanism being affixed to the back side of the support belt;

a pelvic-harness connector having a looped end and a studded end, the looped end being removably connected to the connecting mechanism;

a metallic spring having a bottom end and a top end, the top end being secured to the studded end of the pelvic-harness connector;

a pressing-unit connector having a connecting end and an adjusting end, the connecting end being secured to the bottom end of the metallic spring, the adjusting end having a beginning-threaded end and a stopping-threaded end, the stopping-threaded end beginning midway along the pressing-unit connector;

a foot-pad-pressing unit having a metal sheet and an adjusting means, the metal sheet having a top side, an under side, an upward-facing surface, a downward-facing surface, and at least one centrally located connector receptacle where the adjusting end of the pressing-unit connector is engaged;

a rolling mechanism attached to the downward-facing surface of the metal sheet; and wherein the adjusting means includes an upper turn-bolt and a lower turn-bolt, the upper turn-bolt being positioned on the stopping-threaded end of the pressing-unit connector and adjacent to the top side of the metal sheet, the lower turn-bolt being positioned on the beginning-threaded end of the pressing-unit connector and adjacent to the under side of the metal sheet.

* * * * *